US008603539B2

(12) United States Patent
Srinivas et al.

(10) Patent No.: US 8,603,539 B2
(45) Date of Patent: *Dec. 10, 2013

(54) COMPOSITIONS FOR DRUG DELIVERY

(75) Inventors: Arutla Srinivas, Hyderabad (IN); Harshal P. Bhagwatwar, Hyderabad (IN); Vakati Venkat Arvind, Hyderabad (IN); Saravana Perumal, Hyderabad (IN); Vemula Sathya Narayana, Hyderabad (IN); Mandavalli Srirama Sarveswara Rao, Hyderabad (IN); Venkateswarlu Vobalaboina, Hyderabad (IN); Nookaraju Venkata Sreedharala, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,650

(22) Filed: Oct. 17, 2011

(65) Prior Publication Data

US 2012/0041029 A1 Feb. 16, 2012

Related U.S. Application Data

(63) Continuation of application No. 11/916,685, filed as application No. PCT/US2006/021816 on Jun. 6, 2006, now Pat. No. 8,053,000.

(60) Provisional application No. 60/688,087, filed on Jun. 7, 2005.

(51) Int. Cl.
*A61K 31/4436* (2006.01)
*A61K 47/38* (2006.01)
*A61K 31/203* (2006.01)
*A61P 17/00* (2006.01)
*A61K 9/14* (2006.01)
*A61P 43/00* (2006.01)

(52) U.S. Cl.
USPC .......................................... 424/501; 514/560

(58) Field of Classification Search
None
See application file for complete search history.

(56) References Cited

U.S. PATENT DOCUMENTS

| 4,690,825 | A |   | 9/1987 | Won |
|---|---|---|---|---|
| 5,135,740 | A |   | 8/1992 | Katz et al. |
| 5,145,675 | A |   | 9/1992 | Won |
| 5,292,512 | A |   | 3/1994 | Schaefer et al. |
| 5,316,774 | A |   | 5/1994 | Eury et al. |
| 5,534,261 | A |   | 7/1996 | Rodgers et al. |
| 5,679,374 | A |   | 10/1997 | Fanchon et al. |
| 5,721,275 | A | * | 2/1998 | Bazzano ............... 514/559 |
| 5,725,869 | A | * | 3/1998 | Lo ........................ 424/408 |
| 5,955,109 | A |   | 9/1999 | Won et al. |
| 6,211,250 | B1 |   | 4/2001 | Tomlinson et al. |
| 6,395,300 | B1 |   | 5/2002 | Straub et al. |
| 2002/0010127 | A1 |   | 1/2002 | Oshlack et al. |
| 2003/0232091 | A1 |   | 12/2003 | Shefer et al. |
| 2004/0247632 | A1 |   | 12/2004 | Cotttaneo |
| 2005/0271702 | A1 |   | 12/2005 | Wright et al. |

FOREIGN PATENT DOCUMENTS

| DE | 4111982 A1 |   | 10/1992 |   |
|---|---|---|---|---|
| WO | 91/16930 A1 |   | 11/1991 |   |
| WO | 98/30215 A1 |   | 7/1998 |   |
| WO | WO 98/30215 | * | 7/1998 | ............ A61K 31/20 |
| WO | 00/19996 A1 |   | 4/2000 |   |
| WO | 2004/010988 A1 |   | 2/2004 |   |

* cited by examiner

*Primary Examiner* — Dennis Heyer
(74) *Attorney, Agent, or Firm* — Pergament Gilman & Cepeda LLP; Milagros A. Cepeda; Edward D. Pergament

(57) ABSTRACT

Substantially non-porous polymeric microparticles comprising a hydrophobic polymer and a plasticizer, and containing therein a bioactive or bioinactive agent.

13 Claims, No Drawings

COMPOSITIONS FOR DRUG DELIVERY

INTRODUCTION TO THE INVENTION

The present invention relates to polymeric microparticles containing one or more bioactive or bioinactive agents or combinations thereof. The invention also relates to a dispersion of such particles in a delivery vehicle and the use of such particles and the dispersion for a variety of applications.

Delivery of therapeutic agents for the treatment of disease is primarily through the oral and injectable routes. This is adequate for disease conditions which are systemic or spread out through the body or to areas in the body where the drug can reach by systemic administration such as orally or through injection. But these routes do not address disease conditions of superficial areas of the body such as the skin, vagina, rectum, nose, eye, nail, and others where the disease is localized to these areas. Even though a fraction of the dose administered orally or systemically reaches these areas, a much larger fraction is distributed to the rest of the body resulting in non-target organ toxicity and incomplete efficacy as the required dose does not reach the superficial areas.

Delivery of bioactive and bioinactive agents to and through the skin is an area of drug delivery, which is rapidly gaining importance. This is especially true of active agents that need to be delivered to the surface of the skin or through the skin into the different layers of the skin to treat a variety of disorders such as acne, dermatitis, psoriasis, leprosy, cancers of the skin, and the like, or to have an effect on the aesthetic properties of the skin. Other areas of delivery such as topically, vaginally, rectally, nasally, and other areas which require superficial application of a product for local therapy of disease are also of interest. Compositions available for delivery of active agents to these areas of the body include ointments, creams, gels, lotions, foams, which are easy to administer and have excellent patient acceptability for short duration applications and for non-irritant compounds.

Most of these compositions release the active agents rapidly, resulting in the need for either repeated application, or are washed-off or further result in irritation to the application site because of the irritant nature of the compounds, such as for example retinoids.

Controlled release compositions have been developed to overcome problems of irritancy and repeated application requirements. Such compositions include a porous drug loaded microbead-in-gel delivery system marketed under the trademark RETIN-A MICRO for the delivery of tretinoin as described in U.S. Pat. Nos. 4,690,825, 5,145,675, 5,955,109, 5,135,740, and 5,316,774, among others. These delivery compositions comprise a microsponge delivery system prepared by emulsion polymerization of monomers or co-monomers along with a pore former. The loading of the active ingredient into the microsponge is either through a two-step process involving generation of the porous bead and loading of the porous bead with the active; or through the loading of the drug in the pore former during polymerization. The release of the active from the microsponge is regulated by the porous nature of the beads leading to a drug release by diffusion from the pores.

A disadvantage of the RETIN-A MICRO product is its rough or "gritty' texture when spread onto the skin, due to the nature of microsponges. Many users of the product do not find this sensation pleasing.

Other delivery compositions, which attempt to overcome the above-mentioned drug release problems, include microspheres and liposomes (described in U.S. Pat. Nos. 5,679,374 and 5,534,261) in gel delivery compositions, and the like.

U.S. Pat. No. 5,292,512 discloses microspheres of natural or synthetic polymers or of fatty substances with a melting point higher than about 50° C. filled with at least one active product, characterized in that at least 80% by weight of the microspheres employed have a diameter of between 3 µm and 10 µm. This composition is intended specifically for the delivery of active substances into the sebaceous follicles.

U.S. Patent Application Publication No. 2003/00232091 discloses a composition comprising a plurality of particles or microspheres having retinol encapsulated in hydrophobic matrix materials.

International Application Publication No. WO 00/19996 discloses a microsphere composition for providing modulated release of a retinoid comprising a biodegradable polymer and a biodegradable amphoteric block copolymer having both hydrophilic and hydrophobic groups.

A composition containing substantially non-porous microparticles in a delivery vehicle, whereby the release of the active can be readily modulated through a combination of a hydrophobic polymer and a water-insoluble plasticizer, would provide a solution for a long felt need in local delivery of therapeutics. Such compositions would also be useful in the delivery of active agents orally and by other routes.

SUMMARY OF THE INVENTION

The invention encompasses substantially non-porous polymeric microparticles that contain at least one active agent, which can be a bioactive agent or a bioinactive agent. The size of the microparticles generally ranges from about 0.01 µm to 1 mm. Microparticles can be dispersed in a fluid vehicle for topical application, or can be incorporated into solid formulations for administration orally or by other routes. Dispersions, upon application, form films with microparticles dispersed within, wherein each microparticle functions as a distinct site for the controlled release of bioactive and/or bioinactive agents.

An aspect of the invention includes substantially non-porous polymeric microparticles comprising a hydrophobic polymer and a plasticizer, and containing therein a bioactive or bioinactive agent.

Another aspect of the invention includes a composition comprising:

substantially non-porous polymeric microparticles prepared by dispersing a composition comprising a hydrophilic polymer, a plasticizer, and an active agent in a hydrophilic liquid, and a fluid vehicle.

In yet another aspect, the invention includes a process for preparing substantially non-porous polymeric microparticles, comprising:

providing a solution comprising a hydrophobic polymer, an active ingredient, and a plasticizer in an organic solvent;

adding the solution to a hydrophilic liquid, optionally comprising a stabilizer, to form a mixture;

agitating the mixture to form a plurality of droplets of solution suspended in hydrophilic liquid; and separating substantially non-porous polymeric microparticles.

A further aspect of the invention includes a composition for topical application, comprising:

substantially non-porous polymeric microparticles prepared by dispersing a solution comprising a hydrophobic polymer, a plasticizer, and an active agent in a hydrophilic liquid; and a fluid vehicle comprising water, a viscosity enhancer, and a surfactant.

DETAILED DESCRIPTION OF THE INVENTION

The terms "therapeutic agent", "bioactive agent", "biologically active agent", and "drug substance" are used interchangeably and as used herein are intended to denote substances that have a physiological effect.

The term "bioinactive agent" as used herein is intended to mean a substance that has an adjunctive, protective or cosmetic effect.

The terms "active agent," "active substance," "active ingredient," and "active" are used herein to include any bioactive agent or bioinactive agent that is included in a composition for its effect.

The term "film forming" as used herein intended to mean a substance capable of forming a thin layer on the surface to which it is applied and when exposed to ambient conditions.

The term "percutaneous" as used herein is intended to mean any route of administering an active agent onto, into, or through the skin of a subject so as to achieve one or more of a topical, local, or systemic physiological effect.

The terms "microparticulates," "microparticles," or "microparticulate phase" are used interchangeably and are intended to mean the polymeric microparticles of the invention as described herein.

The term "homogeneously" as used herein is intended to mean that the microparticles are distributed uniformly throughout a delivery vehicle.

The present invention relates to substantially non-porous polymeric microparticles containing one or more bioactive or bioinactive agents or combinations thereof. The invention also relates to a dispersion of such substantially non-porous particles in a delivery vehicle and the use of such particles and the dispersion for a variety of applications. Processes for the preparation of such microparticles and the dispersion are also described.

The present invention relates to a dispersion composition comprising polymeric microparticles for the localized delivery of bioactive or bioinactive agents or combinations thereof. Other routes of administration such as the oral route and other routes where the microparticles and the dispersion compositions would find use are also within the scope of the invention.

The dispersion composition comprises a delivery vehicle having dispersed therein a microparticle phase comprising:
 a hydrophobic polymer;
 optionally, one or more water-insoluble water-swellable polymers;
 one or more water-insoluble plasticizers; and
 one or more active agents.

Optionally, the delivery vehicle can also contain one or more active agents.

The microparticles are unique in that they are prepared from preformed polymers or combinations of preformed polymers which are readily available commercially. Thus, no in-situ polymerization or crosslinking steps are involved in the process of preparation of the microparticles, resulting in microparticles free of residual toxic monomers or catalysts and a manufacturing process with a reduced number of processing steps.

Microparticle preparation and drug loading occurs by a single-step process, resulting in high yields.

In certain embodiments, the microparticles can be collapsible ensuring complete delivery of the active substance without the need for external pressure to ensure complete release of the active. The term "collapsible" as used herein is intended to mean a microparticle phase which may not retain its original shape after completion of drug release. This is different when compared with other prior art microparticulates which do not collapse upon complete drug release, due to the use of a crosslinked polymeric structure.

In another embodiment, the invention includes the use of polymer combinations to provide microparticles through a combination of a hydrophobic polymer optionally with a water-insoluble water-swellable polymer, with a water-insoluble plasticizer, thus allowing the modulation of drug release.

In yet another embodiment, the microparticles are substantially non-porous allowing a better control over the drug release. The term "substantially non-porous" is intended to mean microparticles that can have surface pores, internal pores, or both, but generally lack an interconnected network of pores open to the surface. Such a substantially non-porous product as defined by the porosity and pore volume is obtained by altering the ratio of polymer to plasticizer and controlling the processing parameters during the manufacture of the microparticle phase. Thus, increasing the concentration of the plasticizer in the microparticle composition will generally provide a product with a lower porosity. Further, lower porosity can also be imparted to the microparticle phase through slower drying and at ambient temperatures. An elevated temperature for example can enhance the rate of solvent evaporation, but result in a product with a higher porosity.

Without being bound by any particular theory, the water-insoluble plasticizer allows a reduction in the glass transition temperature of the polymer or polymer combinations used in the present invention, thus providing a microparticle that is not completely rigid as would be expected with the neat polymer or neat polymer combinations. The microparticle thus produced is a species in-between a liquid droplet and a solid particle. It is believed that the use of a water-insoluble plasticizer for the polymer, because of this reduction in glass transition temperature, allows for a substantially non-porous product to be prepared, while at the same time allowing the microparticles to retain enough mechanical strength to keep them in their original shape during further processing and storage.

The microparticles can be of any shape including spherical, oblong, irregular, ellipsoidal and the like. The size of the microparticles generally ranges from about 0.01 µm to 1 mm, or about 0.1 µm to 500 µm, or about 1 µm to 250 µm. The surface area of the microparticles may range from about 0.01 to about 500 m$^2$/g, or about 0.05 to about 50 m$^2$/g. The total pore volume of the microparticles can range from about 0.00001 cm$^3$/g to about 0.1 cm$^3$/g, or about 0.0001 cm$^3$/g to about 0.05 cm$^3$/g and the average pore diameter can range from about 0.1 nm to about 300 nm, or about 1 nm to about 100 nm.

The "total pore volume" is a measure of the porosity that is accessible from the surface of a microparticle, and will not include interior porosity that does not extend, directly or indirectly, to the microparticle surface.

The sizes of the microparticles can be determined using conventional methods of measuring and expressing particle size like Malvern particle size analysis, sieving, light scattering, optical microscopy, image analysis, sedimentation and such other methods known to one skilled in the art. The surface areas and pore volumes of the microparticles can be determined by B.E.T (Brunauer, Emmett and Teller) nitrogen multipoint analysis using instruments such as Quantachrome Autosorb automated gas sorption system, Langmuir multipoint analysis, and other methods known to one skilled in the art.

Particle size distribution information can be obtained from the values $D_{10}$, $D_{50}$, and $D_{90}$, such as can be generated from a Malvern particle size determination. $D_{90}$ as used herein is defined as the size for which 90 volume percent of the particles are smaller than that size given, and $D_{50}$ as used herein is defined as the size for which 50 volume percent of the particles are smaller than that size given. Likewise, $D_{10}$ as used herein is defined as the size for which 10 volume percent of the particles are smaller than that size given.

The formed microparticles are readily dispersed and can be incorporated into fluid delivery vehicles, to allow for ease of local application. The composition has excellent spreadability with a minimum, and frequently an absence, of grittiness. The microparticles, and optionally the delivery vehicle also, when loaded with an active or inactive substance, results in the formation of a delivery system for the active or inactive substance. Such a dispersion upon application to a body forms a film with microparticles dispersed within, wherein each microparticle functions as a distinct site for the controlled release of bioactive or bioinactive agents.

An important aspect of the invention is the modulation of drug release from the composition. The non-porous microparticles provide continuous release of the active agents upon application to a body. The release of the active agent from the composition can be readily modulated through a combination of the hydrophobic polymer (or combination of polymers) and the plasticizer. An increase in the concentration of the plasticizer generally leads to the more rapid release of active substances incorporated into the composition. The incorporation of the plasticizer thus helps in achieving a variety of release profiles by varying the ratios of the polymer and plasticizer.

In a further embodiment of the invention, other bioinactive ingredients such as sunscreens, emollients, moisturizers, anti-wrinkle agents, anti-aging compounds and the like can be added for a protective or cosmetic effect.

The absence of large concentrations of volatile organic solvents such as ethanol and the like in the final product also leads to a composition, which is stable for a prolonged period of time upon storage.

The bioactive or bioinactive agent incorporated into the delivery composition is protected from the atmosphere and has an enhanced chemical stability of unstable actives. Further, the bioactive or bioinactive agent does not come in contact with the skin directly in large amounts and is delivered slowly from the dispersed microparticles through the delivery vehicle, leading to the controlled release of the bioactive or bioinactive agent. This results in a reduced number of applications of the product and also a consequent reduction in the irritation potential of active agents incorporated into the composition. Oily or greasy active substances can be encapsulated by the microparticles such that, on application, they do not leave unpleasant quantities of residues on the skin, and any residue remaining is easy to remove.

These and other aspects and embodiments of the present invention are described in greater detail below.

Biocompatible Polymers: Hydrophobic Polymers.

The polymeric materials useful in the present compositions are those that are biocompatible, substantially insoluble in water and body fluids, and which can be formulated into microparticles. Commercially available polymers are also useful due to their ready availability and compliance with regulatory requirements.

The polymer is a long chain polymer, amorphous, semicrystalline, or crystalline in nature, and can be obtained from a natural, synthetic, or semi-synthetic source.

Examples of the polymers useful in this invention include but are not limited to cellulose derivatives such as ethyl celluloses, methyl celluloses, cellulose acetates and their derivatives, cellulose acetate phthalates, hydroxylpropylmethyl cellulose phthalates, cellulose acylates, cellulose diacylates, cellulose triacylates, cellulose acetates, cellulose diacetates, cellulose triacetates, mono-, di-, and tri-cellulose alkanylates, mono-, di-, and tri-cellulose arylates, mono-, di-, and tri-cellulose alkenylates, methacrylic acid-based polymers such as those sold under the trademark EUDRAGIT, zein, acrylates, aliphatic polyesters, hydrogenated castor oil, locust bean gum, glyceryl monostearate, glyceryl palmitostearate, shellac, and the like. Other classes of polymers, copolymers of these polymers or their mixtures in various ratios and proportions as required are within the scope of this invention without limitation.

It is also possible to include water-soluble polymers such as pyrrolidones, hydroxypropyl methyl celluloses, hydroxypropyl celluloses, chitosans, carrageenan, gelatin, collagen, albumin, fibrin, fibrinogen, betacyclodextrins, polyoxyethylenes, polyoxyethylene-polypropylene block copolymers, polyethylene glycols, polyethylene oxides, and polyvinyl alcohols, in combination with the hydrophobic polymer to modify the hydrophobicity of the polymer.

Water-Insoluble, Water-Swellable Polymers.

The polymer should have the characteristic of biocompatibility and in addition should possess properties of being not only insoluble in water, but also that it should swell in water over a wide range of pH. The presence of such a polymer allows the modulation of release from the microparticles through a combination of the hydrophobicity of the hydrophobic polymer and narrow hydrophilic areas, which are created due to the presence of this polymer. Such polymers can be, for example, low-substituted hydroxylpropyl celluloses (L-HPC), polymethacrylates (Eudragit RL and RS, NE-30D), crosslinked vinylpyrrolidone polymers (commercially available and called “crospovidone”), and the like, and their mixtures in various ratios and proportions, without limitation. Of course, any other polymer which demonstrates such characteristics is also acceptable in the working of this invention.

The term “wide range” as used herein is intended to mean a pH range in which the formulation would be safe for use in human beings, and would generally not be lower than about pH 2 or not higher than about pH 12.

Plasticizers.

Plasticizers suitable for this invention are low molecular mass liquids and solids that when added to a polymer would make it more flexible and less brittle by reducing the glass transition temperature of the polymer. Suitable plasticizers include but are not limited to organic esters such as phthalate esters (diethyl, dibutyl), dibutyl sebacate, isopropyl myristate, citrate esters (triethyl citrate, acetyl triethyl citrate, acetyl tributyl citrate, triacetin), oils and glycerides such as castor oil, acetylated mono glycerides, fractionated coconut oil, stearic and palmitic acids, glycols, glyceryl monostearate, chlorobutanol, benzyl benzoate, and the like. Any plasticizer is acceptable as long as it plasticizes the polymer and is compatible with all components of the composition. Of course, it is to be understood that the plasticizer would be biocompatible and nontoxic to animals.

Delivery Vehicles.

The delivery vehicle should be biocompatible and should not cause any undue irritation to the application site. It should have the capacity to incorporate and hold within its structure large amounts of the microparticulate phase without causing phase separation at the temperature of storage. Further, the delivery vehicle should be immiscible with the dispersed microparticles and have excellent spreadability on application to a surface to rapidly form a film and thus the delivery system of the composition.

Useful hydrophilic fluids for the delivery vehicle include water, glycerol, propylene glycol, sorbitol and other higher alcohols and their mixtures in different proportions. A small percentage of a volatile solvent such as ethanol, acetone, or ethyl acetate and the like can be incorporated to aid processing and is within the scope of the invention.

Viscosity Enhancers.

The viscosity of a fluid delivery vehicle can be enhanced through the addition of viscosity enhancers or gelling agents such as acrylate polymers such as carbopols (including those sold as ULTREZ™), carboxyvinyl polymers, pectin, carrageenan, alginic acid and its salts, gelatin, gums such as xanthan, tragacanth, guar, and chitosan, colloidal silicon dioxide, povidones, polyvinyl alcohols, cetostearyl alcohol, polyethylene oxides, polyoxyethylene-propylene glycol copolymers such as poloxamers, high molecular weight polyethylene glycols, cellulose polymers like hydroxypropyl cellulose, hydroxypropyl methylcelluloses, methylcelluloses, sodium carboxymethyl celluloses, starches, bentonite (VEE-GUM™), propylene carbonate, and other materials. Combinations of these viscosity enhancers can also be used as desired and are within the scope of this invention.

Additives.

Appropriate agents can be added to the composition of the invention to provide the desired properties such as pH, salt concentration, colors and fragrances. Where required, preservatives, antioxidants, opacifiers, emulsifiers, surfactants, emollients, and permeation enhancers can be added to improve the performance of the delivery composition. The use of such materials for formulation of an aesthetically appealing and stable composition for local application is well known to the person who is skilled in the art of preparation of pharmaceutical products. Different classes of compounds from all these categories are included within the scope of the invention without limitation.

Additives can be included in the delivery vehicle for a variety of purposes. Gums or thickening agents can be included to facilitate dispersion and to prevent caking and settling. Examples of these are acacia, tragacanth, alginates, cellulose derivatives (such as methyl cellulose, for example), acrylic acid polymers (Carbopol™), colloidal silicon dioxide (Cab-O—Sil™), polyvinylpyrollidones, and bentonite (Vee-gum™). These will also provide lubricity and a desired viscosity.

Stability of a dispersion can also be enhanced by including a surfactant. The selection of suitable surfactants is well within the skill in the art, from diverse types such as cationic, anionic, and nonionic surfactants. Among the useful surfactants are fatty alcohols, glyceryl esters, and fatty acid esters of alcohols including glycols, sorbitan, sucrose, and cholesterol. Various useful surfactants are obtained by ethoxylating and/or propoxylating ester surfactants, and some examples include, without limitation, polyoxyethylene sorbitan fatty acid esters, polyoxyethylene glyceryl and steroidal esters, and the like.

Aqueous phases can be modified by the addition of agents for increasing or decreasing volatility and for serving as humectants. Examples are alcohols, glycols, polyols such as sorbitol, and sugars such as sucrose, fructose, and dextrose.

Preservatives can desirably be incorporated into the controlled release system for stabilizing actives to protect against the growth of potentially harmful microorganisms. While microorganisms tend to grow in the aqueous phase, microorganisms can also reside in the anhydrous or oil phase. Suitable preservatives for compositions of the present invention include alkyl esters of para-hydroxybenzoic acid like methylparaben and propylparaben, benzoates, hydantoin derivatives, propionate salts, sorbic acid, benzyl alcohol, imidazolidinyl urea, sodium dehydroacetate and a variety of quaternary ammonium compounds. Appropriate preservatives can be selected to satisfy the preservative challenge test and to provide product stability. The preservative can be chosen based on the consideration of possible incompatibilities between the preservative and other ingredients in the release system. Preservatives can be employed in amounts ranging from about 0.01% to about 2% by weight of the composition.

The antioxidants which can be used in the compositions of the present invention should be nonreactive with the components of the formulations, and should be safe for local use. Suitable antioxidants include butylated hydroxytoluene (BHT), butylated hydroxyanisole (BHA), ascorbic acid (vitamin C), propyl gallate, and alpha-tocopherol (vitamin E), although other antioxidants can be used provided they satisfy the above criteria.

Active Agents.

The active agents that are suitable for cosmetic and therapeutic delivery systems are generally those that have one or more of the following characteristics: need to be administered for long periods of time, are highly potent, have a low effective dose, have a short biological active life, and have issues such as irritancy, untoward exposure, or greasiness. Active agents which can be delivered by the compositions of the present invention include any bioactive or bioinactive component which is desired for local application comprising one or more agents such as antioxidants, free radical scavengers, moisturizers, depigmentation agents, reflectants, humectants, antimicrobials, antifungals and antibacterial agents such as beta-lactams, quinolones, ciprofloxacin, norfloxacin, tetracycline, erythromycin, gentamicin, kanamycin, allergy inhibitors, anti-acne agents like retinoids such as tretinoin, isotretinoin, adapalene, tazarotene and azelaic acid, antiaging agents, antiwrinkling agents, antiseptics, analgesics, antihair loss agents, hair growth promoting agents, hair growth inhibitor agents, keratolytic agents, anti-inflammatory agents such as corticosteroids, fresheners, healing agents, anti infective agents, inflammation inhibitors, vasoconstrictors, vasodilators, wound healing promoters, peptides, polypeptides, proteins, deodorants, antiperspirants, skin emollients, skin moisturizers, hair conditioners, hair softeners, hair moisturizers, tanning agens, skin lightening agents, antifungals, depilating agents, counterirritants, poison ivy agents, poison oak agents, burn products, make-up preparations, vitamins, amino acids and their derivatives, herbal extracts, flavinoids, cooling agents, heating agents, skin conditioners, chelating agents, cell turnover enhancers, coloring agents, sunscreens, nourishing agents, moisture absorbers, sebum absorbers, skin penetration enhancers, and the like.

A number of useful active agents are described in U.S. Patent Application Publication No. 2003/00232091, the disclosure of which is incorporated herein by reference. It will be apparent to those skilled in the art that other drug substances and biologicals can be utilized.

Delivery System.

The microparticles of the invention when incorporated into a delivery vehicle form the delivery system of the composition. When an active agent is included in either the microparticulate phase or the delivery vehicle or both, a delivery system is formed which permits modulated delivery of the active agent to the local application site.

The microparticles of the present invention are chemically and biologically inert particles with the active agent held as an impregnant in the microparticles. Release of the active substance is controlled and the desired release profile can be achieved by the use of various concentrations of hydrophobic polymers to the water-insoluble water-swellable polymer or by different ratios of the polymer to the plasticizer. Different systems will thus call for different optimum ranges of polymer ratios or polymer to plasticizer ratios to obtain the most desirable properties of overall formulations.

Preparation of the Microparticles and of the Dispersion Composition.

The microparticles can be formed by any technique known in the art for preparation of such particles (such as those described in S. Benita, Ed., *Microencapsulation: Methods and Industrial Applications*, Marcel Dekker, Inc., New York, N.Y., 1996). Useful techniques include solvent evaporation, coacervation phase separation, spray drying, spray congealing, supercritical fluid extraction, fluidized bed coating, pan coating and other techniques known in the art. In one aspect, solvent evaporation is used to prepare the microparticles of this invention due to its wide spread use and ease of processing.

In general, in a solvent evaporation process for preparation of microparticles, a solution of polymers optionally with a plasticizer and an active substance in an organic solvent is added to the hydrophilic phase containing optionally a stabilizer such as a water-soluble polymer (e.g., polyvinyl alcohol) under stirring followed by removal of the organic solvent. The microparticles are easily recovered by known solid-liquid separation techniques and optionally dried.

In the microparticle preparation, various process parameters and conditions involved in the process can be selected and optimized as a means of controlling the characteristics of the microparticles and the amount of active substance that can be loaded to the microparticles, hence the capacity and the release characteristics of the ultimate product. Process parameters such as temperature, degree of agitation, rate of evaporation of the solvent and like will have impact on the final capacity and release pattern of the microparticles and are well known to a person skilled in the art of preparation of microparticulates.

Once prepared, the microparticulates can be incorporated into the delivery vehicle either as a dry powder to be dispersed into the delivery vehicle or as a wet cake after recovery in the microencapsulation process without drying. Typically, up to about 50%, or up to about 10%, by weight of the microparticulate phase will be incorporated into a delivery vehicle. The amounts incorporated will vary from active agent to active agent, and from composition to composition, and are all within the scope of this invention. Any known techniques for preparation of the final composition are acceptable such as simple mixing, blending, use of a planetary mixer and the like.

The amount of active agent incorporated into the composition depends upon the characteristics of the active agent, the desired release profile and the duration of action intended at the local site of action. There is no critical upper or lower limit of active agent concentration to be incorporated.

In one of the embodiments, the ratio of the hydrophobic polymer to the water-insoluble water-swellable polymer can be varied. The hydrophobic polymer can be used alone, or combined with a water-insoluble water-swellable polymer or optionally in combination with a plasticizer depending upon the desired local drug release profile. The ratios of the three release controlling components can be varied infinitely. Where a faster release profile is required, a higher percentage of the hydrophilic polymer will be used. Where a slower release profile is required, a higher percentage of the hydrophobic polymer will be used. Where a more fluid droplet is required, a higher percentage of the plasticizer will be used. The different ratios and percentages of the three release controlling components to achieve a release profile for a particular active can be determined by a person skilled in the art and are all included herein without limitation.

Similarly, more than one species of microparticles, each loaded with the same or different active agents, can be incorporated into the delivery composition to allow the modulated release of the active or for simultaneous delivery of more than one active from the composition.

In yet another aspect of the invention, delivery of multiple active agents can be achieved through incorporation of multiple microparticulate phases dispersed in the delivery vehicle. Microparticulate phases containing more than one active can be incorporated into the dispersed phase to provide simultaneous delivery of more than one active.

Active agent-containing microparticles can also be incorporated into a delivery vehicle that itself contains one or more active agents, particularly when the different active agents have different desired release profiles.

Mode of Administration.

The compositions of this invention can be part of a kit or device and can be filled into tubes, jars, bottles, aerosol containers, and any other form of packaging that will allow ease of application locally such as to the skin, rectum, vagina, mouth, hair, scalp, nose, and any other such superficial location. The product can also be made as a sterile dispersion and provided in a sealed tube or bottle for use on open wounds, fractures, burns, or infections. The composition is meant to be applied locally, either manually or by using a convenient applicator, for patient compliance and ease of applicability. The dose, number and frequency of applications can be decided by a person skilled in the art of treating local conditions such as a physician, a podiatrist and the like.

The microparticles of the invention can also be used for delivery of active agents by the oral route. For delivery orally, microparticles can be suspended in a palatable fluid such as a syrup or elixir, or incorporated into a solid dosage form. The microparticles can be filled into hard gelatin capsules either alone or in combination with suitable pharmaceutically acceptable excipients. The microparticles can also be converted into tablets and other solid dosage forms. The dispersion compositions of the invention can also be filled into soft gelatin capsules. Suitable pharmaceutically acceptable excipients include diluents such as starch, lactose, dicalcium phosphate, tricalcium phosphate, microcrystalline cellulose, powdered cellulose, sucrose, mannitol, sorbitol, pregelatinized starch and the like or combinations thereof; binders such as acacia, guar gum, tragacanth, gelatin, starch, pregelatinized starch, polyvinyl pyrrolidone, hydroxypropyl cellulose, hydroxyethyl cellulose, hydroxypropyl methylcellulose and the like or combinations thereof; disintegrants such as starch, pregelatinized starch, sodium starch glycolate, croscarmellose sodium, polyvinyl pyrrolidone, crospovidone and the like or combinations thereof; lubricants such as stearic acid, magnesium stearate, zinc stearate and the like or combinations thereof; glidants such as colloidal silicon dioxide; anti-tacking agents such as talc; colorants; solubilizers such as anionic, cationic or zwitterionic and the like or combinations thereof; soft gelatin capsule shell components such gelatin, glycerin, propylene glycol, talc, colorants and water.

The compositions of the present invention can also be used in other fields such as agriculture, controlled release of pesticides, in aquaculture, veterinary drug delivery, and other fields.

Whatever may be the route of administration and the field of application, the general principles of formation of the delivery system will remain.

The following examples further explain certain specific aspects and embodiments of the invention in more detail and are not to be construed as limiting the scope of the invention.

COMPARATIVE EXAMPLE

Preparation of Microparticles Comprising Tretinoin and a Hydrophobic Polymer

| Component | g/Batch |
| --- | --- |
| Dispersed Phase | |
| Tretinoin | 1.5 |
| Ethyl cellulose 10 cps | 75 |
| Methylene chloride | 900 |
| Butylated hydroxytoluene (BHT) | 0.15 |
| Continuous Phase | |
| Polyvinyl alcohol ("PVA"; degree of hydrolysis: 88 mole percent) | 25 |
| Water (q.s.) | 5000 ml |

Manufacturing Process:
1. Ethyl cellulose 10 cps, tretinoin and BHT were dissolved in methylene chloride to form a clear solution.
2. PVA was dissolved in water to form the continuous phase.
3. The solution of step 1 was added to the continuous phase under stirring at 1600 to 1800 rpm.
4. Stirring was continued for 4 hours until methylene chloride was evaporated and microparticles were formed.
5. The microparticles were allowed to settle in the system by gravity, supernatant was decanted and the remaining material was filtered and washed with 500 ml of purified water 3 times at room temperature and dried under vacuum in a vacuum desiccator containing dried self-indicating silica gel.

Particle size was determined using a Malvern Mastersizer. The sample was prepared by adding 20 ml of a 1% aqueous solution of Tween 80 as diluent to 200 mg of microparticles. The microparticles had a particle size distribution of $D_{50}<67$ μm and $D_{90}<117$ μm.

The average surface area (BET), total pore volume (BJH Adsorption) and average pore diameter (BJH Adsorption) of the microparticles was found to be 0.1865 m$^2$/g, 0.000552 cm$^3$/g and 24.18 nm, respectively.

Example 1

Preparation of Microparticles Comprising Tretinoin and a Mixture of a Hydrophobic Polymer with a Water-Insoluble Water-Swellable Polymer

| Component | g/Batch |
| --- | --- |
| Dispersed Phase | |
| Tretinoin | 0.05 |
| Ethyl cellulose 10 cps | 0.5 |
| Methylene chloride | 9.45 |
| BHT | 0.005 |
| Low-substituted hydroxypropyl cellulose (L-HPC) | 0.05 |
| Isopropyl myristate | 0.05 |
| Continuous Phase | |
| PVA (Degree of hydrolysis: 88 mole percent) | 2.5 |
| Water (q.s.) | 500 ml |

The composition was prepared in the same manner as described for the Comparative Example, except for the addition of L-HPC and isopropyl myristate to the methylene chloride solution of step 1.

Example 2

Preparation of Microparticles Comprising Tretinoin and a Combination of a Hydrophobic Polymer and a Water-Insoluble Plasticizer

| Component | g/Batch |
| --- | --- |
| Dispersed Phase | |
| Tretinoin | 0.15 |
| Ethyl cellulose 10 cps | 1.5 |
| Methylene chloride | 28.2 |
| BHT | 0.015 |
| Dibutyl sebacate | 0.15 |
| Continuous Phase | |
| PVA (Degree of hydrolysis: 88 mole percent) | 7.5 |
| Water (q.s.) | 1500 ml |

The composition was prepared in the same manner as described in the Comparative Example, except for the addition of dibutyl sebacate to the methylene chloride solution of step 1.

The microparticles thus obtained had a particle size distribution $D_{50}<50$ μm and $D_{90}<106$ μm, were free from agglomerates and rapidly dispersed when added to water. The average surface area (BET), total pore volume (BJH Adsorption)

and average pore diameter (BJH Adsorption) of the microparticles was found to be 0.2054 m$^2$/g, 0.010765 cm$^3$/g and 102.07 nm.

Example 3

Preparation of Microparticles Comprising Tretinoin and a Combination of a Hydrophobic Polymer and a Water-Insoluble Plasticizer

| Component | g/Batch |
|---|---|
| Dispersed Phase | |
| Tretinoin | 0.05 |
| Ethyl cellulose 10 cps | 0.5 |
| Methylene chloride | 9.45 |
| BHT | 0.005 |
| Isopropyl myristate | 0.05 |
| Continuous Phase | |
| PVA (Degree of hydrolysis: 88 mole percent) | 2.5 |
| Water (q.s.) | 500 ml |

The composition was prepared in the same manner as described in the Comparative Example, except for the addition of isopropyl myristate to the methylene chloride solution of step 1.

Free flowing microparticles thus obtained had a particle size distribution $D_{50}$<74 μm and $D_{90}$<136 μm, were free from agglomerates and rapidly dispersed when added to water.

The average surface area (BET), total pore volume (BJH Adsorption) and average pore diameter (BJH Adsorption) of the microparticles was found to be 0.1696 m$^2$/g, 0.000878 cm$^3$/g and 37.777 nm Example 4

Preparation of Microparticles Comprising Tretinoin Using a High-Speed Homogenizer

| Component | g/Batch |
|---|---|
| Dispersed Phase | |
| Tretinoin | 0.02 |
| Ethyl cellulose 10 cps | 0.5 |
| Methylene chloride | 9.45 |
| Isopropyl myristate | 0.05 |
| BHT | 0.002 |
| Continuous Phase | |
| PVA (Degree of hydrolysis: 88 mole percent) | 2.5 |
| Water (q.s.) | 500 ml |

Manufacturing Process:
1. Ethyl cellulose, isopropyl myristate, tretinoin and BHT are dissolved in methylene chloride to form a clear solution.
2. PVA is dissolved in water to prepare the continuous phase.
3. This solution is added to polyvinyl alcohol solution under homogenization at 11,000 rpm.
4. Stirring is continued using mechanical stirrer till methylene chloride is evaporated and microparticles are formed.
5. The microparticles are allowed to settle in the system, supernatant is decanted, and then remaining material is filtered and washed with 500 ml of purified water 2-3 times at room temperature and dried under vacuum in a vacuum desiccator containing dried self-indicating silica gel.

Example 5

Preparation of Microparticles Comprising Tretinoin and a Combination of a Hydrophobic Polymer and Dibutyl Sebacate Using a High-Speed Homogenizer

| Component | g/Batch |
|---|---|
| Dispersed Phase | |
| Tretinoin | 0.02 |
| Ethyl cellulose 10 cps | 0.5 |
| Methylene chloride | 9.45 |
| Dibutyl sebacate | 0.05 |
| BHT | 0.002 |
| Continuous Phase | |
| PVA (Degree of hydrolysis: 88 mole percent) | 2.5 |
| Water (q.s.) | 500 ml |

A composition for tretinoin microparticles was prepared in the same manner as described in Example 4, except for the addition of dibutyl sebacate in place of isopropyl myristate to the methylene chloride solution of step 1.

Examples 6-9

Preparation of Microparticles Comprising Tretinoin and a Combination of a Hydrophobic Polymer and a Water-Insoluble Plasticizer Using a High-Speed Homogenizer

| | g/Batch | | | |
|---|---|---|---|---|
| Component | Example 6 | Example 7 | Example 8 | Example 9 |
| Dispersed Phase | | | | |
| Tretinoin | 0.05 | 1.5 | 1.17 | 1.5 |
| Ethyl cellulose 10 cps | 0.5 | 75 | 58.33 | 75 |
| Methylene chloride | 9.45 | 900 | 700 | 900 |
| BHT | 0.005 | 0.15 | 1.17 | 0.15 |
| Isopropyl myristate | 0.05 | 7.5 | 5.83 | 15 |
| Continuous Phase | | | | |
| PVA (Degree of hydrolysis: 88 mole percent) | 2.5 | 25 | 19.42 | 25 |
| Water (q.s.) | 500 ml | 5000 ml | 3885 ml | 5000 ml |

The composition was prepared in the same manner as described in Example 4, except for the addition of isopropyl myristate to methylene chloride solution of step 1. The homogenization speed was 6500 rpm in step 3. The microparticles were dried at 20±5° C. at a vacuum of 650-700 mm Hg.

The average surface area (BET), total pore volume and average pore diameter of the microparticles of Example 7 was found to be 0.09899 m$^2$/g, 0.0005905 cm$^3$/g and 23.86 nm.

Example 10

In-Vitro Release of Tretinoin from Microparticles

| Time (hours) | Drug release (%) | | |
|---|---|---|---|
| | Comparative Example | Example 7 | Example 9 |
| 1 | 1.1 | 22.2 | 31.1 |
| 2 | 1.6 | 31.2 | 42.1 |
| 4 | 2.6 | 40.3 | 56.3 |
| 6 | 3.5 | 45.4 | 65.3 |
| 8 | 4.5 | 49.2 | 73.1 |

The microparticles were subjected to a drug release study using a VanKel dissolution cell. It contains an enhancer cell assembly, a dissolution flask and a paddle. The enhancer cell assembly is a Teflon assembly with adjustable volume and a screw cap to retain the membrane.

Microparticles equivalent to 15 mg of tretinoin were placed in the enhancer cell and a Millipore 0.45 μm PVDF (polyvinylidene difluoride) membrane filter was placed over the cell. The washer was placed over the membrane and retaining ring was screwed on. The enhancer cell was placed in the dissolution flask containing 200 ml of dissolution medium (0.5% w/w hydroxypropyl β-cyclodextrin in 0.1 N sodium hydroxide). The temperature of the flask was maintained at 34° C.±0.5° C. and the medium in the flask was stirred at 100 rpm. Samples were analyzed for tretinoin by HPLC.

Example 11

Preparation of a Dispersion of Drug-Loaded Microparticles in a Delivery Vehicle Made Using Carbopol Microparticles:

| Component | g/Batch |
|---|---|
| Dispersed Phase | |
| Tretinoin | 1.5 |
| Ethyl cellulose 10 cps | 75 |
| Methylene chloride | 900 |
| BHT | 0.15 |
| Isopropyl myristate | 7.5 |
| Continuous Phase | |
| PVA (Degree of hydrolysis: 88 mole percent) | 25 |
| Water (q.s.) | 5000 ml |

Microparticles in Delivery Vehicle:

| Ingredient | g/Batch |
|---|---|
| Microparticles | 95.37 |
| Carbopol 974 P* | 22.5 |
| Glycerin | 75 |
| Propylene glycol | 82.5 |
| Sodium EDTA | 0.75 |
| Sorbic acid | 1.5 |
| Benzyl alcohol | 7.5 |
| Cyclomethicone and dimethicone copolyol | 30 |
| Triethanolamine | 12 |
| PPG-20 methyl glucose ether distearate | 30 |
| Polyoxyethylene (20) sorbitan monooleate | 0.45 |
| Water (q.s.) | 1500 ml |

*Polymer of acrylic acid, cross-linked with allyl ethers of sucrose or pentaerythritol Manufacturing Process:
1. Disodium EDTA was dissolved in water (previously heated to 50±10° C.).
2. The solution was cooled to room temperature.
3. Sorbic acid was dissolved in propylene glycol under stirring.
4. Glycerin and benzyl alcohol were added to solution of step 3 and mixed uniformly.
5. The solution of step 2 was added to solution of step 4 and mixed uniformly.
6. Carbopol was dispersed in solution of step 5 under stirring to obtain uniform dispersion.
7. Microparticles (previously dispersed in water) were added to the dispersion of step 6 and stirred to get uniform dispersion.
8. Ingredients 8 and 10 were mixed in polyoxyethylene (20) sorbitan monooleate.
9. The mixture of step 8 was added to dispersion of step 7 with stirring.
10. Triethanolamine was added to the mixture of step 9 for neutralization.

The pH of the composition was observed to be 3.5 before addition of triethanolamine and 5.52 after addition of triethanolamine Example 12

Preparation of a Dispersion of Drug-Loaded Microparticles in a Delivery Vehicle Made Using Colloidal Silicon Dioxide

| Ingredient | Concentration (%) |
|---|---|
| Microparticles of Example 8 | 5.8 |
| Colloidal silicon dioxide | 6 |
| Glycerin | 5 |
| Propylene glycol | 5.5 |
| Sodium EDTA | 0.05 |
| Sorbic acid | 0.1 |
| Benzyl alcohol | 0.5 |
| Cyclomethicone and dimethicone copolyol | 2 |
| PPG-20 methyl glucose ether distearate | 2 |
| Polyoxyethylene (20) sorbitan monooleate | 0.03 |
| Water | q.s. to make 100 |

The composition was prepared in a similar manner to that in Example 11, except that colloidal silicon dioxide was dispersed in the solution of step 5 under stirring to obtain a uniform dispersion.

Example 13

Preparation of a Dispersion of Drug-Loaded Microparticles in a Delivery Vehicle Made Using a Mixture of Sodium Carboxymethyl Cellulose and Hydroxyethyl Cellulose

| Ingredient | g/Batch |
|---|---|
| Microparticles of Example 7 | 19.14 |
| Sodium carboxymethyl cellulose | 4.5 |
| Hydroxyethyl cellulose | 1.5 |
| Glycerin | 15 |
| Propylene glycol | 27.5 |
| Sodium EDTA | 0.25 |
| Sorbic acid | 0.5 |
| Benzyl alcohol | 1.5 |
| Cyclomethicone and dimethicone copolyol | 10 |
| PPG-20 methyl glucose ether distearate | 20 |
| Polyoxyethylene (20) sorbitan monooleate | 3 |
| Water (q.s.) | 300 ml |

The composition was prepared in a similar manner as in Example 11, except that in step 6 sodium CMC and hydroxyethyl cellulose were dispersed in the solution of step 5 under stirring to obtain a uniform dispersion.

Example 14

Preparation of a Dispersion of Drug-Loaded Microparticles in a Delivery Vehicle Made Using Sodium Carboxymethyl Cellulose

| Ingredient | g/Batch |
|---|---|
| Microparticles of Example 7 | 2.34 |
| Sodium carboxymethyl cellulose | 0.8 |
| Glycerin | 2 |
| Propylene glycol | 2.2 |
| Sodium EDTA | 0.02 |
| Sorbic acid | 0.04 |
| Benzyl alcohol | 0.2 |
| Polyoxyethylene (20) sorbitan monooleate | 0.12 |
| Water (q.s.) | 40 |

Manufacturing Process:
1. Disodium EDTA was dissolved in previously heated water.
2. The solution was cooled to room temperature.
3. Sorbic acid was dissolved in propylene glycol under stirring.
4. Glycerin and benzyl alcohol were added to solution of step 3 and mixed uniformly.
5. The solution of step 2 was added to solution of step 4 and mixed uniformly.
6. Sodium carboxymethyl cellulose was dispersed in solution of step 5 under stirring to obtain uniform dispersion.
7. Microparticles (previously dispersed in water) were added to the dispersion of step 6 and stirred to get a uniform dispersion.

Example 15

Preparation of Microparticles Comprising Tazarotene

| Ingredient | g/Batch |
|---|---|
| Drug Solution | |
| Tazarotene | 0.1 |
| BHT | 0.1 |
| Ethyl cellulose 10 cps | 5 |
| Isopropyl myristate | 0.5 |
| Methylene chloride | 30 |
| Polyvinyl alcohol Solution | |
| PVA (Degree of hydrolysis: 88 mole percent) | 0.75 |
| Water q.s. to | 150 ml |

Manufacturing Process:
1. Water was heated to 80° C.-90° C.
2. Polyvinyl alcohol was dissolved in water to form a clear solution.
3. The solution was cooled to room temperature and filtered.
4. BHT and tazarotene were dissolved in methylene chloride under stirring to form a clear solution.
5. Ethyl cellulose was added to the solution of step 4 and stirred to form a clear solution.
6. Isopropyl myristate was added to the solution of step 5 and stirred.
7. The solution of step 6 was added to the solution of step 3, homogenized at 6500 rpm and stirred at 200 to 250 rpm to allow for evaporation of methylene chloride.
8. Supernatant liquid was decanted and the residue was filtered. The residue was washed with water and filtered to obtain microparticulates.
9. The microparticulates were dried in a dessicator containing activated silica with vacuum.

Free flowing microparticles thus obtained had a particle size distribution $D_{50}$<52.44 µm and $D_{90}$<190.1 µm, were free from agglomerates and rapidly dispersed when added to water.

Examples 16-24

Preparation of Microparticles Comprising Different Active Ingredients

| | Active | Particle Size Distribution (µm) | | |
|---|---|---|---|---|
| Example No. | Ingredient | $D_{10}$ | $D_{50}$ | $D_{90}$ |
| 16 | Terbinafine | 9.36 | 30.6 | 72.92 |
| 17 | Erythromycin | 7.68 | 18.72 | 48.8 |
| 18 | Fluconazole | 9.74 | 26.6 | 74.34 |
| 19 | Salicylic acid | 12.69 | 37.36 | 89.09 |
| 20 | Oxybenzone | 7.18 | 19.28 | 53.85 |
| 21 | Naproxen | 15.18 | 43.76 | 101.67 |
| 22 | Menthol | 8.56 | 20.49 | 53.79 |

-continued

| Example No. | Active Ingredient | Particle Size Distribution (μm) | | |
|---|---|---|---|---|
| | | $D_{10}$ | $D_{50}$ | $D_{90}$ |
| 23 | Camphor | 8.57 | 20.15 | 50.1 |
| 24 | Adapalene | 9.7 | 21.27 | 43.06 |

Compositions of Example 16 to Example 24 were prepared in the same manner as in Example 15 except that tazarotene was replaced by the corresponding active ingredient (0.1 g/batch) in step 4.

Example 25

In Vitro Drug Release from Microparticle in Gel-Based Systems of Example 8 and Example 9

| Time (hours) | Drug Release (%) | | |
|---|---|---|---|
| | Example 8 | Example 9 | Retin-A Micro ® |
| 1 | 29.5 | 33 | 30.38 |
| 2 | 50 | 49 | 48.66 |
| 4 | 76 | 63 | 73.6 |
| 6 | 87 | 83 | 86.48 |
| 8 | 98 | 90 | 94.34 |

The microparticulates of Example 8 and Example 9 in gel-based systems were subjected to a drug release study using a VanKel dissolution cell. It contains an enhancer cell assembly, a dissolution flask and a paddle. The enhancer cell assembly is a Teflon assembly with adjustable volume and a screw cap to retain the membrane.

About 200 mg of composition was placed in the enhancer cell and a Millipore 0.45 μm PVDF (polyvinylidene difluoride) membrane filter was placed over the cell. The washer was placed over the membrane and retaining ring was screwed on. The enhancer cell was placed in the dissolution flask containing 200 ml of dissolution medium (0.5% w/w hydroxypropyl β-cyclodextrin in 0.1 N sodium hydroxide). The temperature of the flask was maintained at 34° C.±0.5° C. and the medium in the flask was stirred at 100 rpm. Samples were analyzed for tretinoin by HPLC.

A comparative study was performed in similar manner for release of tretinoin from the commercial product Retin-A Micro® topical gel (0.1%).

Examples 26-28

Microparticle Compositions Comprising Varying Amounts of Active Ingredient

| Ingredient | g/Batch | | |
|---|---|---|---|
| | Example 26 | Example 27 | Example 28 |
| Drug Solution | | | |
| Tretinoin | 0.01 | 0.015 | 0.018 |
| BHT | 0.001 | 0.0015 | 0.0018 |
| Ethyl cellulose 10 cps | 0.5 | 0.5 | 0.5 |
| Isopropyl myristate | 0.05 | 0.05 | 0.05 |
| Methylene chloride | 12.5 | 12.5 | 12.5 |
| Polyvinyl alcohol solution | | | |
| PVA (Degree of hydrolysis: 88 mole percent) | 0.38 | 0.38 | 0.38 |
| Water q.s to | 75 ml | 75 ml | 75 ml |

Manufacturing process: The microparticles of Examples 26-28 are prepared by the following process:
1. Polyvinyl alcohol is dissolved in heated water with stirring to form a clear solution.
2. It is cooled to room temperature and filtered.
3. BHT and tretinoin are dissolved in methylene chloride under stirring to form a clear solution.
4. Ethyl cellulose is added to the solution of step 3 and stirring is continued to form a clear solution.
5. Isopropyl myristate is added to solution of step 4 and stirred.
6. The components of mixture of step 5 are homogenized at 11000 rpm and stirred at 750 to 1000 rpm to allow for evaporation of solvent.
7. The supernatant liquid is decanted to obtain a residue containing microparticles.
8. The microparticles are washed with water three times and filtered.
9. The microparticles are dried in a dessicator till loss on drying reached less than about 1%.

Example 29

Comparative Irritancy Study

The microparticles in gel-base system of Example 11 was compared with commercially available Retin-A Micro® (0.1% tretinoin gel; Batch No. 4KM973) for irritation potential. Twenty-two healthy volunteers (18 male and 4 female) in the age range of 20-35 years participated in the study. About 0.1 g of the composition of Example 11 was applied to the right forearm and the commercial composition was applied the left forearm of the volunteer and left for 10 minutes without further treatment. Subject observations were recorded immediately after application and at several intermediate points up to 10 minutes. The irritation intensity/stinging was recorded on a 0-4 scale.

| Intensity of irritation | Score |
|---|---|
| No irritation | 0 |
| Slight irritation | 1 |
| Mild irritation | 2 |
| Significant irritation | 3 |
| Severe irritation | 4 |

The composition of Example 11 did not cause any significant irritation and was easily spreadable. The difference in the composition of Example 11 and the commercial composition was not found to be significant with respect to the irritation potential.

| | Frequency of Score* | |
|---|---|---|
| Score | Composition of Example 11 | Retin-A Micro ® |
| 0 | 19 | 18 |
| 1 | 1 | 2 |
| 2 | 1 | 1 |
| 3 | 1 | 1 |
| 4 | 0 | 0 |

*Total number of subjects = 22

Example 30

Preparation of Microparticles Comprising Varying Concentrations of Tretinoin

| Ingredient | Amount (g/Batch) | | |
|---|---|---|---|
| Dispersed phase | | | |
| Tretinoin | 0.05 | 0.125 | 0.25 |
| Ethyl cellulose 5 cps | 0.5 | 0.5 | 0.5 |
| Isopropyl myristate | 0.05 | 0.05 | 0.05 |
| Methylene chloride | 9.45 | 9.37 | 9.25 |
| Continuous phase | | | |
| PVA (Degree of hydrolysis: 88 mole percent) | 2.5 | 2.5 | 2.5 |
| Water q.s. | 500 ml | 500 ml | 500 ml |

The compositions are prepared in a similar manner as in Example 4 except that BHT is not added in step 1.

Example 31

Comparative Dermal Irritation Study of Gel-Based Composition of Example 11 with RETIN-A® MICRO in New Zealand White Rabbits A dermal irritation study was performed to compare relative irritation potential of gel-based composition of Example 11 ("Test") and Retin-A® Micro ("Reference"; Batch 4KM973). Six male New Zealand white rabbits of age between 10 to 15 months and weight in the range of 2 to 3 Kg were used in the study. 2% w/v sodium lauryl sulphate was used as positive control (Control 1) and a composition with all components (without tretinoin) similar to Example 11 was used as negative control (Control 2). The hair on the backs of the rabbits was clipped and approximately 0.5 g of Test or Reference or Control 2 was placed on a gauze patch and was applied to the skin site. Separate gauze patches containing Test, Reference and Control 2 were applied on the back. The patches were moistened with 0.5 ml physiological saline after application. 0.5 ml of Control 1 was injected into a fourth gauze patch after applying the patch on the skin. The patches were removed after 24 hours.

The test and control items were categorized based on the Primary Dermal Irritation Index (PDII). The PDII was determined as the ratio of total irritation score (TIS) and total number of observations. The TIS was calculated by adding the subtotal values for erythema and edema. The subtotal values for erythema and edema were separately calculated by adding the irritation scores at 25, 48 and 72 hours post-application. The following scoring criteria were used as described in the literature (S. C. Gad et al., *Acute Toxicology Testing: Perspectives and Horizons*, The Telford Press, Inc., Caldwell, N.J., 1988):

| Skin reaction | Score |
|---|---|
| No erythema/edema | 0 |
| Very slight erythema/edema | 1 |
| Slight erythema/edema | 2 |
| Moderate erythema/edema | 3 |
| Severe erythema/edema | 4 |

| PDII | Interpretation |
|---|---|
| 0 | Nonirritant |
| 0 to 0.5 | Negligible irritant |
| 0.5 to 2 | Mild irritant |
| 2 to 5 | Moderate irritant |
| 5 to 8 | Severe irritant |

The PDII of the test composition was found to be comparable to the reference and both of the products can be categorized as mild irritants.

| Product | PDII |
|---|---|
| Test | 1.06 |
| Reference | 1.13 |
| Control 1 | 0.44 |
| Control 2 | 0 |

The invention claimed is:

1. A composition for topical application, comprising:
substantially non-porous polymeric microparticles, prepared by (i) providing a solution comprising a hydrophobic polymer, a plasticizer, and an active agents; (ii) adding the solution to a hydrophilic liquid to form substantially non-porous polymeric microparticles containing surface pores, internal pores, or both, but having substantially no internal porosity connecting with the surface; and
a fluid vehicle comprising water, a viscosity enhancer, and a surfactant.

2. The composition of claim 1, wherein microparticles have a surface area ranging from about 0.01 to about 500 $m^2/g$.

3. The composition of claim 1, wherein microparticles have a total pore volume from about 0.00001 $cm^3/g$ to about 0.1 $cm^3/g$.

4. The composition of claim 1, wherein a hydrophobic polymer comprises a cellulose derivative.

5. The composition of claim 1, wherein a plasticizer comprises an organic ester, an oil, a glyceride, or a mixture of two or more thereof.

6. The composition of claim 1, wherein a plasticizer comprises an organic ester.

7. The composition of claim 1, wherein a hydrophobic polymer comprises ethyl cellulose.

8. The composition of claim 1, wherein a hydrophilic liquid comprises water.

9. The composition of claim 1, wherein an active agent comprises a drug substance.

10. The composition of claim 1, wherein an active agent comprises tretinoin.

11. The composition of claim 1, wherein an active agent comprises tazarotene.

12. The composition of claim 1, wherein a plasticizer is water-insoluble.

13. The composition of claim 1, wherein a solution comprises an organic solvent.

* * * * *